United States Patent [19]

Gazzani

[11] Patent Number: 5,352,389
[45] Date of Patent: Oct. 4, 1994

[54] COMPOSITION FOR THE CLEANING OF THE SKIN, SCALP AND HAIR

[75] Inventor: Giovanni Gazzani, Appiano Gentile, Italy

[73] Assignee: Crinos Industria Farmacobiologica SpA, Guardia, Italy

[21] Appl. No.: 909,836

[22] Filed: Jul. 7, 1992

[30] Foreign Application Priority Data

Jul. 8, 1991 [IT] Italy ................. MI91 A 001885

[51] Int. Cl.$^5$ ............... C11D 7/32; C11D 7/40; C11D 7/42
[52] U.S. Cl. ............... 252/544; 252/546; 252/548; 252/156; 252/174.12; 252/DIG. 5; 252/DIG. 12; 252/DIG. 13
[58] Field of Search ............ 252/544, 546, 548, 156, 252/DIG. 5, DIG. 13, 174.12, DIG. 12

[56] References Cited

U.S. PATENT DOCUMENTS

| | | | |
|---|---|---|---|
| 3,309,321 | 3/1967 | McMaster | 252/544 |
| 3,708,435 | 1/1973 | Starkman | 252/544 |
| 3,778,502 | 12/1973 | Aubin | 514/564 |
| 3,832,310 | 8/1974 | Grand | 252/544 |
| 4,235,898 | 11/1980 | Watanabe et al. | 252/544 |
| 4,436,653 | 3/1984 | Jacobson et al. | 252/547 |
| 4,438,024 | 3/1984 | DelGreco et al. | 252/545 |
| 4,451,385 | 5/1984 | Tavss et al. | 252/132 |
| 4,707,291 | 11/1987 | Thom et al. | 252/174.12 |
| 4,749,507 | 6/1988 | Varco | 252/91 |
| 4,784,798 | 11/1988 | Geke et al. | 252/544 |
| 5,077,040 | 12/1991 | Bermann et al. | 424/70 |
| 5,096,622 | 3/1992 | Simion et al. | 252/548 |
| 5,223,179 | 6/1993 | Connor et al. | 252/548 |

FOREIGN PATENT DOCUMENTS

| | | |
|---|---|---|
| 0077630 | 4/1983 | European Pat. Off. . |
| 0077630 | 4/1983 | European Pat. Off. . |
| 0097810 | 1/1984 | European Pat. Off. . |
| 0455185A2 | 11/1991 | European Pat. Off. . |
| 2401752 | 7/1973 | Fed. Rep. of Germany . |
| 2401752 | 7/1974 | Fed. Rep. of Germany . |
| 3541485A1 | 5/1987 | Fed. Rep. of Germany . |
| 865747 | 5/1941 | France . |
| 865747 | 5/1941 | France . |
| 2277859 | 7/1975 | France . |
| 2277859 | 7/1975 | France . |
| 54223 | 3/1969 | Luxembourg . |

OTHER PUBLICATIONS

H. Janistyn: "Handbuch der Kosmetika und Riechstoffe", 2nd edition, *1973, vol. III: Die Korperpflegemittel, pp. 239–240.

*Primary Examiner*—Paul Lieberman
*Assistant Examiner*—E. Higgins
*Attorney, Agent, or Firm*—Nikaido Marmelstein Murray & Oram

[57] ABSTRACT

The invention discloses compositions in the form of aqueous solutions or O/W emulsions for the cleaning of skin, scalp and hair, characterized in that they contain from 0.5 to 5% w/v of at least one water soluble organic base chosen in the group consisting of low molecular weight saturated aliphatic alkylamines, their hydroxy derivatives, low molecular weight primary alkylenediamines, basic aminoacids. Said water soluble organic base are buffered at pH 7-9. The cleaning efficacy of said preparations may be increased by adding lipases in a quantity ranging from 0.1 to 1% w/v. According to a further embodiment of the invention, said compositions can be comprised of detergents in a quantity not exceeding 4% w/v. The compositions are endowed of the property of cleaning the skin in a delicate manner, with a good local tolerability.

21 Claims, No Drawings

COMPOSITION FOR THE CLEANING OF THE SKIN, SCALP AND HAIR

This invention relates to a composition in the form of an aqueous solution or O/W emulsion for the cleaning of skin, scalp and hair endowed with a very good skin tolerability.

It is believed worthwhile to review in short here the criteria that have been so far followed in compounding synthetic detergents in products for the cleansing and hygiene of the body in the effort to avoid, or at least to reduce the problems of cutaneous tolerability that arise on using these substances.

The outlook will help to understand better the different approach to this problem being proposed in this invention.

It is well known that the use of synthetic detergents in products for personal care is quite old and probably can be dated back to the first decades of this century. The large diffusion of these products occurred in more recent times, when formulations such as shampoos, foambaths, syndets, etc., i.e. products intended to meet the many needs of personal care, were introduced on the market.

Besides having an immediate success from the consumers, these products were and are found advantageous also for the manufacturers, since their industrial costs compare favourably with those of classic soaps and compositions thereof.

The most significant advantages afforded by such formulations can be condensed in the following: better yield, lower costs as already said and better handling characteristics. Further, the circumstance that the pH of the preparations can be made neutral, or corrected to values even lower than this resulted in a much better dermal compatibility in comparison to that obtainable with classics soaps.

Anyway, as hereabove already noted, these detergents did still show some important adverse effects on the skin, that can be catalogued as follows:

Excessive delipidation of epidermis.
Cutaneous dryness, roughness and chapped skin.
Local sensitization and/or irritation, relevant in particular for eyelids and eye mucosa.
Reactive seborrhea, in particular on the scalp.

On this issue it must be said that the research of the field is ever endeavouring in synthetizing new surfactants with still improved dermal compatibility.

Anyway amongst these substances nowadays are already available, as it is known to the practised artisan, compounds such as amphoterics and nonionics, and in particular amongst the latter the oxyethylene derivatives, which have very good characteristics as to skin tolerability.

At the same time the expert of the field is well aware that cleaning compositions compounded only with such substances wouldn't still represent the right solution to the above referred problems, as the cleaning efficacy of amphoterics and nonionics is well known to be lower than that of other detergents, such as those of the anionic type.

Hence in the hypothesis hereabove made the quantities of surfactants should be necessarily higher than those found usual in cleaning formulations.

Such a situation would in a first instance imply the risk of loosing, at least in part, the advantageous skin tolerability of amphoterics and nonionics, as adverse cutaneous effects are known to be directly dependent on the quantity of surfactant.

Further it is believed that these products would be hampered by higher unit costs, in relation to the higher value of the detergents therein contained.

Accordingly the cleaning compositions made available by the manufacturers nowadays consist almost invariably of mixtures of different substances, compounded according to the following basic criteria:

a. Associating surface active agents belonging to different classes, and more in detail combining anionics with amphoterics and noionics, in order to meet the requirement of a good cleaning action together with an acceptable local tolerability.

b. Associating ionic detergents with other substances able to develop a protective action on the skin such as proteins, collagen and saccharide derivatives, superratting agents, etc.

In trying to approach a new solution of the problem of dermal compatibility, the idea that appears the most simple and worthwhile of a thorough investigation is whether it is practicable to bring about a significant reduction in the quantities of detergents without loosing at the same time the required cleaning effect.

In that case the relevant formulations may advantageously comprise compounds not endowed per se with an appreciable cleaning activity, but at the same time having such peculiar properties as to bring about a synergism with the true surfactants, so that it could still ensure the required detergent effect.

The above concept has been moreover already applied recently in this art.

To cite an example it may be herein mentioned the European Patent Application n. 84200088.7, that discloses detergent compositions wherein the overall quantity of surface active agents is less than that generally reputed to be the standard effective requirement. At the same time there are therein comprised thickening agents, that are known already in the art to be able to increase the stability of the emulsion formed when the formulation comes into contact with soil.

On this issue worth reminding here is that it is known since long in the state of the art (see for due reference the paper by D. C. Stevenson ' Mechanism of detergency' published on J. Soc. Cosm. Chem. vol. XII 1961, pages 353–370) that emulsion stability is one of the important steps in the mechanism of detergency. The solution that has been instead given here in order to solve, or anyway to ameliorate the same above referred to problems of skin tolerability, starts from the experimental observation that aqueous or O/W emulsion compositions containing the water soluble organic bases herebelow referred to, buffered at a pH comprised between 7 and 9, are able to remove cutaneous organic soil.

As shown by examples 1-3 the observed cleaning effect can be attributed to a direct local formation of quantities of soaps between said bases and the free fatty acids that are contained in organic soil.

Furthermore the above referred pH range of said formulations is such as these soaps would be prevented from being harmful to the skin.

A further confirmation of this peculiar mechanism of detergency comes from the observation that the cleaning effect increases by adding to the solution small quantities of lipases, i.e. enzymes endowed with lipolytic activity, as it will be herebelow detailed.

Hence according to a first object of the invention these compositions are characterized in that they contain from 0.5 to 5% w/v of buffered water soluble organic bases belonging to one or more of the following groups or classes: low molecular weight saturated aliphatic alkylamines and their hydroxy derivatives, primary $C_2$–$C_3$ alkylenediamines, basic aminoacids.

It is of importance to stress here that said water soluble bases have no surface active properties or are otherwise emulsifiers or detergents.

This can be confirmed with a very simple experiment made on the relevant aqueous solutions, as by example those containing basic aminoacids, which even after thorough shaking don't bring about any foam formation.

This hints further that the use of such compounds as active ingredients of detergent compositions wasn't at all foreseeable.

For each of the hereabove mentioned groups the preferred substances for the purposes of the invention are listed further on here below.

The formulations of the invention may contain at least one water soluble base or otherwise a corresponding mixture with one or more compounds belonging to the above referred to classes.

An essential feature of such compositions is that they don't contain fatty acids, i.e. both unsaturated and saturated aliphatic monocarboxylic acids with a straight chain with at least 4 carbon atoms (see F. D. Gunstone ' An introduction to the chemistry of fats and fatty acids' Chapman & Hall Ltd. London, pages 2–21, in particular Table I at page 3 ).

Further, any acidic ingredient to be eventually added can be previously changed to its corresponding salt, since otherwise it employs the water soluble organic bases for neutralizing the negative charge.

In this way the pH is lowered and the cleaning performance of the formulations, as shown in example 2, is negatively affected.

Alternatively, said acidic ingredients may be added as such and then eventually neutralized with the same water soluble organic bases, provided that the actual quantity of the latter substances should be in excess of the amount required for the neutralization, so that the solution pH should be in the foreseen alkaline range.

The minimum required excess is of 0.5% ( w/v, calculated on the whole composition ).

The overall quantity of said bases must not obviously exceed the upper limit (5%) of the w/v variation range hereabove set forth.

A further essential feature of this invention is that the new formulations in relation to the delicate cleaning action aimed at must not comprise organic solvents of skin soil, such as for instance ethyl alcohol or mineral oil, that are often found in cosmetic products.

The low molecular weight saturated aliphatic alkylamines and their corresponding hydroxy derivatives that are useful for the purposes of the present invention are primary, secondary, tertiary aliphatic saturated alkylamines, and corresponding hydroxy derivatives, characterized in that, with the exception of N-methyl glucamine, they contain no more than 4 carbon atoms for each alkyl chain wherein no more than three carbon atoms are set on the longest alkyl chain(s).

The preferred water soluble aliphatic alkylamines are selected from the following: methylamine; ethylamine; propylamine; isopropylamine; dimethylamine; diethylamine; dipropylamine; diisopropylamine; trimethylamine; triethylamine; tripropylamine; N-propyldimethylamine; N-propyldiethylamine.

The hydroxy derivatives of the above reported alkylamines are chosen from the group consisting of the following : monomethanolamine; monoethanolamine; isopropanolamine, 2-amino 2-methyl propanol; 2-amino, 2-methyl, 1,3-propandiol; 2-amino, 2-hydroxymethyl 1,3-propanediol; dimethanolamine; diethanolamine; diisopropanolamine; dipropanolamine; N-methyl, 2-aminoethanol; N-ethyl, 2-aminoethanol; N-methyl, 3-aminopropanol; N-methyl, 2-aminopropanol; N-ethyl, 3-aminopropanol; N-methyl, 2-amino, 1,3-propandiol; N-ethyl, 2-amino, 1,3 propandiol; N-methyl glueamine; trimethanolamine; triethanolamine; tripropanolamine; triisopropanolamine; N-hydroxypropyl, N-di-hydroxyethylamine; N-dimethylaminoethanol; N-diethylaminoethanol; N-dimethylaminopropanol; N-diethylaminopropanol.

The low molecular weight primary $C_2$–$C_3$ alkylenediamines are ethylenediamine and propylenediamine.

The preferred basic aminoacids are hystidine, arginine, lysine and hydroxylisine. Particularly preferred amongst basic aminoacids is lysine.

The preferred pH is comprised between 7–8.5.

The pH of the solutions or O/W emulsions containing said water soluble organic bases is then corrected within the range 7–9 or the preferred 7–8.5 by addition of small quantities of low molecular weight saturated aliphatic mono $C_1$–$C_3$) carboxylic acids or both saturated and unsaturated di-, tri-, tetra- ($C_4$–$C_6$) carboxylic acids, being characterized in that they are soluble or at least partially soluble in water and are devoid of surface-active properties.

For the same purpose also strong inorganic acids can be advantageously employed, as such or admixed with the former organic acids.

Addition of said acid(s) can be effected by using directly the pure substance in liquid or in solid form or otherwise also the related concentrated aqueous solutions, depending on the overall quantity of the amine(s) being comprised in the formulation.

Such low molecular weight carboxylic organic acids are preferably chosen from the group consisting of formic acid, acetic acid, tartaric acid, succinic acid, maleic acid, malic acid, lactic acid, fumaric acid, citric acid, and ethylenediaminotetraacetic acid.

The above compositions comprising further the usual excipients well known to the man of this art (see further on here below ) are intended for the cleaning of the skin and can be made available as cleansing lotions and creams.

To said compositions may optionally be added lipolytic enzymes of animal origin (i.e. pancreatic lipase and the like ), vegetable origin (i.e. wheat germ lipase and the like) or bacterial origin (i.e. pseudomonas lipase, candida cilindracea lipase and the like) in order to increase the detergent effect.

The quantity of said enzymes, which activity should be however one of a Pharmacopeia grade or the like, is comprised between 0.1 and 1% w/v.

In relation to the notorious limited stability of said proteins in aqueous solutions, they must be admixed with the cosmetic formulations just before use.

To this effect there can be applied known packaging techniques. For instance the enzyme in powder form can be stored in a sealed dispenser cap, so that it can be admixed with the compositions only when required.

The stability of the enzyme in the solution can be improved by binding the protein to known substrates, such as agarose, which products are found already in commerce. According to a further object of this invention, whereas the composition must develop a more exhaustive detergent action, as in the case of shampoos and liquid bath preparations notoriously used to clean at the same time also scalp and hair, said water soluble bases can be admixed with surfactant(s), or mixtures thereof, wherein the overall quantity of the further component(s) is not higher than 4% w/v.

Such surfactants may be of the anionic, non ionic or of the amphoteric type.

It has been surprisingly found that the mixture of said substances with the water soluble amines of the invention in the pH range hereabove set forth, in the presence of sebum shows a synergism in the cleaning effect comparable to that given by formulations containing almost three times the same quantity of detergents.

It has been moreover observed that in the presence of lipases the quantity of detergents can be even more diminuished.

It is worthwhile mentioning here in order to illustrate further how low is the figure of 4%w/v of detergent content that in the prior art (as it is for instance learnt from the book' Cosmetic Science and Technology' by E. Sagarin, pages 418–419), the quantities of detergents referred to as being effective in products for personal care usually comprised between 16% and 20% by weight of the composition.

Since said water soluble organic bases are very well tolerated when dissolved in aqueous solutions or O/W emulsions at the concentrations and pH herein foreseen, and moreover the quantity of surfactants that is eventually added according to the above referred further embodiment is very limited, the formulations of the invention don't bring about any whatsoever relevant drawback in that it concerns cutaneous tolerability.

The compositions of the invention may further contain the usual ingredients well known already to the practised artisan, as for instance the following: thickening agents, such as alginic acid, carrageenan, pectin, soluble starch, guar gum, gelatin, agar agar, carbopol, cellulose derivatives; polypeptides ; organic water- insoluble polymers which function as mild abrasives, such as whole starch, cellulose, peat, chitin, chitosan, lignin, etc.; perfumes, preservatives.

Wherein said compositions are in the form of creams, they may contain also suitable vehicles in order to increase their viscosity, such as for instance cetostearilic alcohol, etc.

The invention is illustrated by the examples herebelow given, that by no means should be construed as laying down undue limitations on the objects of the application.

Example 1 concerns an experiment wherein it is given evidence that the water soluble bases are able to bring about an emulsion with sebum. It has been noted herein already that emulsification is a very important step in the mechanism of detergency.

In example 2 it is shown that if the fatty material doesn't comprise fatty acids, the water soluble bases don't form O/W emulsion at a significant extent.

In example 3 it is reported a demonstration of the detergent effect of compositions according to the first object of the invention, i.e. containing the buffered water soluble bases only. The concentration adopted is of 0.5% and the pH corrected at 8.5 by means of citric acid. In said demonstration a piece of cotton fabrics, priorly soiled with artificial sebum admixed with a quantity of red scarlet dye, is soaked in the solutions of said bases. By a point score system it is then evaluated the quantity of scarlet red dye released in solution following emulsification with artificial sebum.

Example 4 features the better effectiveness of lysine as compared to arginine.

Example 5 gives a demonstration of the synergism of the detergent activity of surfactants when admixed with said water soluble bases at the above referred to pH ranges in the presence of sebum.

The results therefrom evidence that the synergistic mixture affords a significant reduction in the quantity of surfactants required to give the same cleaning effect, so that the related amount can be lowered of about two thirds of that requested in the absence of said bases.

In Example 6 it is given a further confirmation of the synergistic effect. More in particular it is shown that solutions containing 2% w/v sodium lauryl sulphate (SLES) and 0.5 % of the water soluble bases have the same detergent effect than 6% SLES solutions.

It is therein evidenced that the local tolerability of the 2% pure detergent solution, being evaluated in the experimental model of the rabbit's eye, it is quite the same as that of the formulations containing the same quantity of surfactants added of 0.5% of the water soluble bases.

EXAMPLE 1

Emulsions brought about by the water soluble bases of the invention in the presence of sebum.

A certain amount of artificial sebum was prepared according to P. Sosis et Alii, Soaps/Cosmetics/Chemical Specialities 49, July, 32, 1973. The sebum had the following composition (percentages are by weight ): palmitic acid 10%, stearic acid 5%, oleic acid 10%, linoleic acid 5%, coconut oil 15%, paraffin 10%, spermaceti 15%, olive oil 20%, squalene 5%, cholesterol 5%.

Separately were then prepared 0.5% w/v aqueous solutions of the following water soluble bases: ethylamine; methylamine; dimethylamine; diisopropylamine; N-propyldiethylamine; triethylamine; tripropylamine; ethylenediamine; monoethanolamine; diethanolamine; 2-amino, 2-hydroxymethyl, 1,3-propanediol; diethylaminoethanol; N-methyl 2-aminopropanol+N-methyl, 3-aminopropanol ( in the ratio of about 1:1); N-methyl, 2-amino, 1,3-propandiol; tripropanolamine; methylgucamine; arginine.

The pH was then corrected to the value of 8 by addition of glacial acetic acid. In 150 ml beckers were placed 15 ml of said artificial sebum and then 35 ml of each of the preceding 17 water soluble base solutions. After thorough agitation and mixing, it was observed the forming of a milky-like emulsion.

EXAMPLE 2

Demonstration that the water soluble bases of the invention are not able to form emulsions with fatty material wherein free fatty acids are not comprised.

In 150 ml beckers were placed 15 ml of vaseline oil ( i.e. a mixture of liquid hydrocarbons ) and then 35 ml of each of the same 17 water soluble base solutions reported in the preceding example 1. After thorough agitation and mixing it was observed that in each of the samples under assay there was very little tendency to the forming of emulsions.

EXAMPLE 3

Demonstration of the detergent effect of the water soluble bases of the invention. Artificial soil was prepared by mixing g 12 of olive oil with 1 g of oleic acid. The mixture was then added of 0.12 g red scarlet dye ( overall percentage by weight: 0.91% ). The oily phase was then dissolved in 600 ml of methylene chloride. Separately were prepared squared strips (4 cm×4 cm) of clean cotton fabrics, that were then soaked for 2 hours in the organic solution.

The strips were then dried at room temperature for 24 hours in the dark and then transferred into 150 ml beckers, each containing a quantity (100 ml ) of 0.8 % w/v of one of the water soluble bases of the preceding example 1, buffered at pH 8.5 with a 10% w/v citric acid solution. the solutions were thermostatted at 37C and agitated by means of a glass rod for 10 minutes. The aqueous phase was then recovered.

Since solubilization of red scarlet dye was accompanied by the forming of a milky-like emulsion, the color intensity of each solution could not be evaluated by the aid of an instrument and then was made on a subjective scale using the following point score system.

To the most coloured sample solution was given the conventional score of 4, wherein to the reference blank ( distilled water ) was given a null score.

Amongst the test solutions it was then chosen a sample having an intermediate red colour between the two hereabove referred to limits and was assigned of a score of 2.

It was found that the solutions had an individual score comprised between 2 and 4. More in particular it was observed that whereas the solutions containing the aliphatic amines and aliamines gave a score value comprised between 2 and 3, those containing hydroxyalkylamines, N-methyl glucamine and arginine gave a higher score, comprised between 3 and 4.

With the same experimental design it was checked the cleaning efficacy of the above compositions on lowering the corresponding pH. It was then found that the score value remained substantially unaltered by decreasing pH down to 7. Below this value it was assessed a significant drop of performance. For instance at pH 6.5 the score of the test solutions of the group of aliphatic amines and aliamines was found to be lower than 2, whereas that of the solutions of the latter group was found lower than 3.

EXAMPLE 4

Demonstration of the better detergent effectiveness of lisine as compared to arginine. Aqueous solutions of each of these bases were prepared by dissolving 1g of each compound in 100 ml of distilled water and correcting then the pH to about 8.5 with concentrated phosphoric acid. Each of the solutions was then poured, as from the preceding example 3, in one 150 ml becker where it had been previously placed a piece of cotton fabric treated as therein described. After thermostatting with mixing as hereabove reported, it was observed that the colour intensity of the lysine solution was higher than that of arginine.

EXAMPLE 5

Demonstration of the synergistic effect in detergent activity obtained by mixing the water soluble bases with surfactants in the pH range 7-9 and in the presence of sebum.

The following solutions were prepared:
Saccharose monolaurate (SM): 3%, 6% and 9% w/v solutions corrected to pH 7 with sodium hydroxide solution.
Laurylether sodium sulphate 3-OE ( SLES ): 1,5%, 3%, 4,5% solutions.

100 ml aliquots of 6% SM solution and 3% SLES solution were respectively added of a same quantity of 1% w/v solutions containing each of the bases of example 1.

The solutions were then brought to pH 8 with glacial acetic acid.

To each of the solutions thus obtained was then added a strip of cotton fabric formerly treated as described in example 3. The procedure followed in order to bring about dye solubilization was the same as that reported in the preceding example.

In order to provide color intensity reference standards, each of the above said solutions containing different concentrations of pure SM or SLES were added of a strip of cotton fabric soiled as detailed in example 3 and then processed in the same way hereabove referred to.

At the end of the experiment it was found that the color intensity of samples containing 3% SM together with 0.5% of water soluble base was comparable with that of the solution containing 9% SM.

In the same way the color intensity of samples containing 1.5% SLES together with 0.5% of water soluble base was quite similar to that of the solution containing 4.5% SLES.

EXAMPLE 6

Confirmation of the synergistic detergent effect of example 5 thereof and demonstration of the local tolerability of the compositions according to the further object of the invention.

Solutions containing respectively 6% w/v SLES, 2% SLES and 2% SLES together with 0.5% of each of the bases listed in example 1, buffered at pH 8 with glacial acetic acid were prepared.

The results that were obtained by using the method described under example 3 showed that the solutions containing SLES admixed with said water soluble bases had a cleaning efficacy comparable to that given by 6% w/v SLES solutions.

It was observed that the irritating effect evaluated by putting in the rabbit's eye New Zealand rabbits, one for each tested solution) three drops of each of the solutions 2% SLES+0.5% base was the same as that provided by pure 2% SLES solution.

Such results allow the conclusion that the compositions according to this further embodiment of the invention afford a substantial reduction of the detergent content of the related formulations with quite evident benefits as to local tolerability.

EXAMPLE 7

| Skin cleaning lotion | |
|---|---|
| lysine (base) | 0.8% |
| xanthan gum | 0.5% |
| sodium carrageenan | 0.2% |
| glycerine | 0.5% |
| perfumes, preservatives and waters enough to | 100 ml |
| citric acid 10% solution enough to pH 8.2. | |

EXAMPLE 8

| Mild skin cleansing lotion | |
|---|---|
| tromethamine (base) | 2.0% |
| glycerine | 5.0% |
| plant proteins | 1.0% |
| perfumes, preservatives and water enough to EDTA crystals enough to pH 8. | 100 ml |

EXAMPLE 9

| Amphoteric shampoo | |
|---|---|
| sodium carrageenan | 0.2% |
| rice starch | 0.2% |
| lysine (free base) | 0.5% |
| cocamido propyl betaine | 1.0% |
| sodium lauroylsarcosinate | 1.0% |
| sodium cocoamphoyglycinate | 1.0% |
| perfume, preservatives and water enough to succinic acid 5% w/v solution enough to 7.5. | 100 ml |

EXAMPLE 10

| Tonic shampoo | |
|---|---|
| PEG 150 distearate | 0.3% |
| triethanolamine | 1.0% |
| laurylether sulfate sodium salt | 1.0% |
| cocamide | 1.0% |
| cocamido propyl betaine | 0.3% |
| perfume, preservatives and water enough to conc. phosphoric acid enough to pH 7.7. | 100 ml |

EXAMPLE 11

| Revitalizing shampoo | |
|---|---|
| carboxyvinyl resin sodium salt | 1.0% |
| peat powder 100 mesh | 2.0% |
| methylglucamine | 2.0% |
| sodium dilauryl (7) OE citrate | 1.0% |
| sodium alkyl sulfonate | 1.0% |
| keratin lysate | 1.0% |
| polysorbate 80 | 1.0% |
| perfume, preservatives and water enough to conc. acetic acid enough to pH 7.8. | 100 ml |

EXAMPLE 12

| Shower bath preparation | |
|---|---|
| oat starch | 3.0% |
| N-methyl, 2-amino, 1,3-propandiol | 1.0% |
| triethanolamine laurylether sulfate | 1.5% |
| cocamido propyl betaine | 1.0% |
| dioctyl sodium sulphosuccinate | 1.0% |
| milk albumine | 0.5% |
| perfume, preservatives and water enough to glacial acetic acid enough to pH 8. | 100 ml |

EXAMPLE 13

| Hand cleansing cream | |
|---|---|
| arginine (free base) | 1.0% |
| sodium lauroylsarcosinate | 1.0% |
| sodium methyl cocoiltaurate | 1.0% |
| cetostearylic alcool | 2.0% |

| Hand cleansing cream (continued) | |
|---|---|
| perfume, preservatives and water enough to EDTA crystals, enough to pH 7.5. | 100 ml |

EXAMPLE 14

| Face cleansing cream | |
|---|---|
| neutralized pectin | 1.0% |
| lysine (base) | 4.5% |
| sodium cocoil-glutamate | 1.0% |
| poloxamer$^R$ | 1.0% |
| saccarose monolaurate | 1.0% |
| perfume, preservatives and water enouth to conc. phosphoric acid enough to pH 7.5. | 100 ml |

EXAMPLE 15

| Hair shampoo | |
|---|---|
| sodium alginate | 1.5% |
| purified cellulose | 0.5% |
| methylglucamine | 0.5% |
| magnesium stearate laurylether sulfate | 1.0% |
| saccharose monolaurate | 1.0% |
| potassium coco-hydrolized animal proteins | 1.0% |
| perfumes, preservatives and water enough to lactic acid 10% w/v sol. enough to pH 8. | 100 ml |

EXAMPLE 16

| Nonionic shampoo | |
|---|---|
| sodium carboxymethylcellulose | 1.0% |
| keratine powder | 3.0% |
| N-methyl,3-aminopropanol + N-methyl-2-aminoipropanol | 1.0% |
| polysorbate 20 | 2.0% |
| polyglucose laurate | 1.0% |
| cocamide | 1.0% |
| perfume, preservatives and water enough to EDTA crystals enough to pH 8.5. | 100 ml |

EXAMPLE 17

| bath foam composition | |
|---|---|
| N-di-hydroxyethylamine | 3.5% |
| sodium $C_{14}$–$C_{16}$ sulfonate | 3.5% |
| laurylmonosulfosuccinate disodium salt | 0.5% |
| decylpolyglucoside | 0.5% |
| perfume, preservatives and water enough to conc. phosphoric acid enough to pH 8.2 | 100 ml |

EXAMPLE 18

| Skin cleaning composition | |
|---|---|
| pancreatic lipase USP grade* | 0.2% |
| lysine | 1.0% |
| perfume, preservatives and water enough to citric acid 10% w/v solution enough to pH 8. | 100 ml |

(*the enzyme is stored in a dispensing cap).

EXAMPLE 19

| Hair shampoo | |
|---|---|
| pancreatic lipase USP grade* | 0.8% |
| triethanolamine | 3.0% |
| dioctyl sodium sulphosuccinate | 0.5% |
| Sodium carboxymethylcellulose | 0.4% |
| perfume, preservatives and water enough to | 100 ml |
| glacial acetic acid enough to pH 7.8. | |

(*see example 18).

I claim:

1. Detergent composition in the form of an aqueous solution or an O/W emulsion for the cleaning of the skin, scalp and hair, said composition being substantially free of fatty acids and organic solvents of the skin soil, said composition comprising at least one surfactant in an overall quantity not higher than 4% w/v and being of the amphoteric, anionic or nonionic type, at least one water soluble organic base buffered at pH 7-8.5 in a quantity ranging from 0.5 to 5% w/v, said water soluble organic base being chosen from one or both of the following groups:

Low molecular weight primary, secondary or tertiary saturated aliphatic alkylamines and their corresponding hydroxy derivatives characterized in that, with the sole exception of the compound N-methyl glucamine, said substances have no more than 4 carbon atoms for each alkyl chain, wherein no more than three carbon atoms are set on the longest straight alkyl chain(s); and Basic aminoacids;

characterized in that an acidic ingredient is added to the composition and then neutralized with said water soluble organic base, the quantity of said at least one base being in excess of the amount required for neutralization, so that the solution pH should be in the alkaline range of 7-8.5.

2. Detergent composition in the form of an aqueous solution or an O/W emulsion for the cleaning of the skin, scalp and hair, said composition being substantially free of fatty acids and organic solvents of the skin soil, said composition comprising at least one surfactant in an overall quantity not higher than 4% w/v and being of the amphoteric, anionic or nonionic type, at least one water soluble organic base buffered at pH 7-8.5 in a quantity ranging from 0.5 to 5% w/v, said water soluble organic base being chosen from one or both of the following groups:

Low molecular weight primary, secondary or tertiary saturated aliphatic alkylamines and their corresponding hydroxy derivatives characterized in that, with the sole exception of the compound N-methyl glucamine, said substances have no more than 4 carbon atoms for each alkyl chain, wherein no more than three carbon atoms are set on the longest straight alkyl chain(s); and Basic aminoacids;

said composition being characterized further in that any other acidic ingredient to be added to said composition is previously changed to its corresponding salt.

3. A detergent composition in the form of an aqueous solution or an O/W emulsion for the cleaning of the skin, scalp and hair, said composition being substantially free of fatty acids and organic solvents of the skin soil, said composition comprising at least one surfactant in an overall quantity not higher than 4% w/v and being of the amphoteric, anionic or nonionic type, at least one water soluble organic base buffered at pH 7-8.5 in a quantity ranging from 0.5 to 5% w/v, said water soluble organic base being chosen from one or both of the following groups: -Low molecular weight primary, secondary or tertiary saturated aliphatic alkylamines and their corresponding hydroxy derivatives characterized in that, with the sole exception of the compound N-methyl glucamine, said substances have no more than 4 carbon atoms for each alkyl chain, wherein no more than three carbon atoms are set on the longest straight alkyl chain(s), said low molecular weight saturated aliphatic alkylamines being chosen from the group consisting of methylamine; ethylamine; propylamine; isopropylamine; dimethylamine; diethylamine; dipropylamine; diisopropylamine; trimethylamine; triethylamine; tripropylamine; N-propyldimethylamine; and N-propyldiethylamine; said hydroxy derivatives of the low molecular weight saturated aliphatic alkylamines being chosen from the group consisting of monomethanolamine; monoethanolamine; isopropanolamine, 2-amino, 2-methyl, propanol; 2-amino, 2-methyl, 1,3-propandiol; 2-amino 2-hydroxymethyl 1,3-propandiol; dimethanolamine; diethanolamine; diisopropanolamine; dipropanolamine; N-methyl, 2-aminoethanol; N-ethyl, 2-aminoethanol; N-methyl, 3-aminopropanol; N-methyl, 2-aminopropanol; N-ethyl, 3aminopropanol; N-methyl, 2-amino, N-ethyl, 2-amino, 1,3 propandiol; N-methyl glucamine; trimethanolamine; triethanolamine; tripropanolamine; triisopropanolamine; N-hydroxypropyl, N-di-hydroxyethylamine; N-dimethylaminoethanol; N-diethylaminoethanol; N-dimethylaminopropanol; N-diethylaminopropanol, said water soluble base being a hydroxy derivative of an aliphatic alkylamine, methylgucamine or a basic aminoacid; and Basic aminoacids chosen from the group consisting of hystidine, arginine, lysine and hydroxylisine;

characterized in that an acidic ingredient is added to the composition and then neutralized with said water soluble organic base, the quantity of said at least one base being in excess of the amount required for neutralization, so that the solution pH should be in the alkaline range of 7-8.5.

4. Detergent composition according to claim 1 or 2, characterized in that said excess of said at least one base is at least 0.5% (w/v, calculated on the whole composition) and the overall quantity of said at least one base doesn't exceed 5% w/v.

5. Detergent composition according to claim 1 or 2, characterized in that said low molecular weight saturated aliphatic alkylamines are chosen from the group consisting of the following:

methylamine; ethylamine; propylamine; isopropylamine; dimethylamine; diethylamine, dipropylamine; diisopropylamine; trimethylamine; triethylamine; tripropylamine; N-propyldimethylamine; and N-propyldiethylamine.

6. Detergent composition according to claim 1 or 2, characterized in that the hydroxy derivatives of the low molecular weight saturated aliphatic alkylamines are chosen from the group consisting of the following: monomethanolamine; monoethanolamine; isopropanolamine, 2-amino, 2-methyl, propanol; 2-amino, 2-methyl, 1,3-propandiol; 2-amino 2-hydroxymethyl 1,3-propandiol; dimethanolamine; diethanolamine; diisopropanolamine; dipropanolamine; N-methyl, 2-aminoethanol; N-ethyl, 2-aminoethanol; N-methyl, 3-aminopropanol; N-methyl, 2-aminopropanol; N-ethyl, 3-aminopropanol; N-methyl, 2-amino, 1,3-propandiol; N-ethyl, 2-amino, 1,3 propandiol; N-methyl glucamine; trimethanolamine; triethanolamine; tripropanolamine; triisopropanolamine; N-hydroxypropyl, N-di-hydroxyethylamine; N-dimethylaminoethanol; N-diethylaminoethanol; N-dimethylaminopropanol; N-diethylaminopropanol.

7. Detergent composition according to claim 1 or 2, characterized in that the basic aminoacids are chosen from the group consisting of the following: hystidine, arginine, lysine and hydroxylisine.

8. Detergent composition according to claim 1 or 2, characterized in that the water soluble bases are the hydroxy derivatives of aliphatic alkylamines, methylgucamine and basic aminoacids.

9. Detergent composition according to claim 1 or 2, wherein the basic aminoacid is lysine.

10. Detergent composition according to any one of claims 1, 2 and 3, wherein said composition further comprises at least one lypolytic enzyme of animal origin, of vegetable origin or of bacterial origin.

11. Detergent composition according to claim 10, characterized in that said lipase is pancreatic lipase.

12. Detergent composition according to any one of claims 1, 2 and 3, wherein said composition further comprises at least one lipolytic enzyme of animal origin, of vegetable origin or of bacterial origin, said lipase being pancreatic lipase.

13. Detergent composition according to any one of claims 1, 2 or 3, wherein said composition further comprises at least one member of the group consisting of thickening agents, organic water insoluble polymers which function as mild abrasives, and suitable vehicles to increase viscosity when said composition is in the form of a cream.

14. A method of cleaning skin comprising contacting skin with a detergent composition according to any one of claims 1, 2 or 3.

15. A method according to any one of claims 1, 2 or 3, wherein said composition is in the form of a lotion or a cream.

16. A method of cleaning hair, scalp or body comprising contacting a detergent composition according to any one of claims 1, 2 or 3, with hair, scalp or body.

17. A method according to claim 16, characterized in that said composition is in the form of a shampoo or a liquid bath preparation.

18. A detergent composition according to claim 8, wherein the basic aminoacid is lysine.

19. A detergent composition as recited in claim 10 or claim 12 wherein said lipolytic enzyme comprises pancreatic lipase.

20. A detergent composition as recited in claim 10 or claim 12 wherein said lipolytic enzyme comprises wheat germ lipase.

21. A detergent composition as recited in claim 10 or claim 12 wherein said lipolytic enzyme comprises pseudomonas lipase or candida cilindracea lipase.

* * * * *